United States Patent [19]

Osborne

[11] Patent Number: 5,762,917
[45] Date of Patent: Jun. 9, 1998

[54] METHOD AND COMPOSITION FOR CLEANSING WOUNDS WITH MINIMAL CYTOTOXICITY FOR MINIMAL SCARRING

[75] Inventor: David W. Osborne, The Woodlands, Tex.

[73] Assignee: Virotex Corporation, The Woodlands, Tex.

[21] Appl. No.: 624,309

[22] Filed: Mar. 26, 1996

Related U.S. Application Data

[63] Continuation-in-part of Ser. No. 313,714, Sep. 27, 1994, abandoned.

[51] Int. Cl.$^6$ .................. A61K 31/765; A61K 7/50
[52] U.S. Cl. .................. 424/78.06; 424/78.07
[58] Field of Search .................. 424/78.07, 78.06

[56] References Cited

U.S. PATENT DOCUMENTS

| | | | |
|---|---|---|---|
| Re. 29,909 | 2/1979 | Kurtz | 252/89 R |
| 2,970,073 | 1/1961 | Prange . | |
| 3,579,465 | 5/1971 | Schmolka | 252/316 |
| 3,997,458 | 12/1976 | Kurtz | 252/89 R |
| 4,300,555 | 11/1981 | Kopito | 128/248 |
| 4,326,977 | 4/1982 | Schmolka | 252/106 |
| 4,474,753 | 10/1984 | Haslam et al. | 424/78 |
| 4,664,906 | 5/1987 | Sipos | 424/49 |
| 4,678,664 | 7/1987 | Schmolka | 424/65 |
| 4,782,047 | 11/1988 | Benjamin et al. | 514/174 |
| 4,919,837 | 4/1990 | Gluck | 252/106 |
| 4,954,338 | 9/1990 | Mattox | 424/78 |
| 4,983,595 | 1/1991 | Benjamin et al. | 514/174 |
| 5,227,161 | 7/1993 | Kessler | 424/94.4 |
| 5,275,805 | 1/1994 | Nabi et al. | 424/54 |
| 5,292,525 | 3/1994 | Brenden et al. | 424/601 |
| 5,335,373 | 8/1994 | Dangman et al. | 2/161.7 |
| 5,357,636 | 10/1994 | Dresdner et al. | 2/161.7 |
| 5,370,815 | 12/1994 | Kessler | 252/106 |
| 5,527,530 | 6/1996 | Simmons et al. | 424/78.06 |
| 5,547,662 | 8/1996 | Khan et al. | 424/78.06 |

*Primary Examiner*—Peter F. Kulkosky

[57] ABSTRACT

A method and composition for cleansing a wound comprising irrigating the wound with a surfactant, an antiseptic, and a preservative mixed in an aqueous solution having minimal cytotoxicity, and thereby cleansing the wound with minimal scarring.

11 Claims, No Drawings

4,762,917

METHOD AND COMPOSITION FOR CLEANSING WOUNDS WITH MINIMAL CYTOTOXICITY FOR MINIMAL SCARRING

FIELD OF THE INVENTION

The present invention relates to methods and compositions for cleansing wounds which promote optimal wound healing wherein the wound-cleansing compositions have minimal cytotoxicity. This application is a continuation-in-part of U.S. application Ser. No. 08/313,714 filed Sep. 27, 1994 now abandoned.

BACKGROUND OF THE INVENTION

Proper wound cleansing is an integral step in all wound treatment regimens. For treatment of minor cuts and abrasions, cleansing is most often effected with soap and water, hydrogen peroxide, or rubbing alcohol. While these cleansers may be effective in disinfecting the wound, they are biologically aggressive and result in destruction of tissue in the wound site. This destruction of tissue, referred to as cytotoxicity, hinders the wound healing process and often increases the degree of scarring which appears over the healed wound area. While it is essential to remove exogenous debris and potential pathogens from the wound site, the wound cleanser must be as non-cytotoxic as possible in order to promote the most favorable conditions for wound healing.

SUMMARY OF THE INVENTION

The present invention comprises methods and compositions for cleansing wounds with minimal scarring wherein said wound-cleansing compositions have minimal cytotoxicity and comprise a low-cytotoxic surfactant, a low-cytotoxic antiseptic, and a non-cytotoxic preservative, mixed in an aqueous solution.

In one embodiment of the present invention, the surfactant comprises a polyoxyethylene, polyoxypropylene block polymer. In another embodiment the antiseptic comprises benzalkonium chloride, benzethonium chloride, camphorated metacresol, camphorated phenol, hexylresorcinol, methylbenzethonium chloride, or phenol. In still another embodiment the preservative comprises sodium benzoate, glydant, (also referred to as DMDM hydantoin) potassium sorbate, chlorhexidine digluconate or a combination thereof.

DETAILED DESCRIPTION OF THE INVENTION

The present invention is directed to novel methods for cleansing wounds with minimal scarring and compositions for cleansing wounds with minimal scarring wherein the non-cytotoxic, wound-cleansing compositions comprise a surfactant, an antiseptic, and a preservative, and wherein said compositions are highly effective at promoting wound healing. The compositions of the present invention comprise topical solutions which are suitable for use in cleansing all types of wounds, particularly wounds associated with minor cuts and abrasions. The compositions are mixed in an aqueous solution to provide a minimally cytotoxic solution for cleansing wounds.

The non-cytotoxic surfactant used in the present invention removes exogenous debris such as dirt and grease from the wound via surface activity. The non-cytotoxic surface active agents tend to be nonionic surfactants, especially those that have high molecular weights such as the block copolymers. These surface active agents quickly migrate to the dirt or grease interface and lift the exogenous debris from the wound upon irrigation with the wound cleansing composition. The low-cytotoxic antiseptic destroys microbial and bacterial pathogens in the wound site, and the preservative agent prevents the growth of bacteria and fungi that might contaminate the unused portion of the product. A preservative must be present for a multiple use product container.

The surfactant used in the present invention may comprise a polyoxyethylene, polyoxypropylene block polymer which is commonly referred to as a "Poloxamer". The preferred Poloxamer is polyoxyethylene or polyoxypropylene block polymer of ethylene diamine. The surfactant preferably comprises about 1 to about 20 weight percent of the total composition.

The antiseptic used in the present invention may comprise an aryl-substituted halide or aryl-substituted alcohol such as benzalkonium chloride, benzenethonium chloride, camphorated metacresol, camphorated phenol, hexylresorcinol, methylbenzethonium chloride, or phenol. The antiseptic preferably comprises about 0.05% to 0.5% by weight of the total composition, except for camphorated phenol and camphorated metacresol. For camphorated phenol, the preferred weight percentages are about 8% to 12% camphor and about 3% to 7% phenol. For camphorated metacresol, the preferred weight percentages are about 3% to 12% camphor and about 1% to 4% metacresol.

The preservative may comprise sodium benzoate, glydant, (also referred to as DMDM hydantoin) potassium sorbate, or chlorhexidine digluconate, or a combination thereof. The preservatives preferably comprise about 0.05% to 0.5% by weight of the total composition.

The surfactant, antiseptic, and preservative used in the present invention may be combined with a carrier system such as water, saline, buffer solution, or other aqueous solution suitable for topical application to wounds. The aqueous solution comprises the remainder of the total composition.

To further illustrate the present invention, but not by way of limitation, the following examples are provided.

EXAMPLE 1

In the development of a preferred embodiment, various combinations of preservatives and antiseptics were tested in order to develop a low toxicity wash. Those experiments were performed as follows.

A monolayer of L-929 mouse fibroblast cells was grown to confluency and overlaid with Minimum Essential Medium supplemented with serum, antibiotics, neutral red, and 2% agarose. The test article, a 0.5 cm×0.5 cm piece of 725871H as a positive control, a filter paper disc saturated with 0.1 ml of 0.9% SC as a filter disc control, and a 1.0 cm length piece of UP-1 as a negative control were placed on the solidified overlay surface. Following incubation for 24 hours, the culture was macroscopically examined for evidence of cell decolorization to determine the zone of cell lysis. Any decolorized zone present was examined microscopically to confirm cell lysis.

The greater the zone of lysis, the greater the cytotoxicity of the wound wash formulation. For six unique formulations using 4% Poloxamer 188 as a cleanser, the following zones of lysis were determined. Cytotoxicity was tested using the agarose overlay cytotoxicity test.

| 0.1% Hexylresorcinol | | | 0.1% Benzalkonium Chloride | | |
| --- | --- | --- | --- | --- | --- |
| 0.2% chlorhexidine digluconate | 0.2% sodium benzoate | 0.2% potassium sorbate | 0.2% chlorhexidine digluconate | 0.2% sodium benzoate | 0.2% potassium sorbate |
| 7 mm | 13 mm | 14 mm | entire flask | entire flask | 12 mm |

From this testing, chlorhexidine gluconate is the preservative that gives unexpected low toxicity, while hexylresorcinol is the antiseptic agent that provides unexpectedly low cytotoxicity. Other embodiments of the invention are listed in the formulations below.

EXAMPLE 2

Eight different 4 weight percent Pluronic® surfactants (BASF Corporation, Parsippany, N.J.) were tested in combination with 0.1% hexylresorcinol and 0.2% chlorhexidine gluconate. These formulations were tested with regard to physical appearance and if of the desired appearance (clear single phase solution over the ambient temperature range) then subsequently tested for cytotoxicity. Cytotoxicity was tested using the agarose overlay test described in Example 1.

| Generic Name | BASF Tradename | Appearance | Zone of Lysis |
| --- | --- | --- | --- |
| Meroxapol 105 | Pluronic 10R-5 | Phase Separation | — |
| Meroxapol 174 | Pluronic 17R-4 | Phase Separation | — |
| Poloxamer 124 | Pluronic L44 | Phase Separation | — |
| Poloxamer 184 | Pluronic L64 | Phase Separation | — |
| Poloxamer 188 | Pluronic L68 | Clear Single Phase | 7 mm |
| Poloxamer 237 | Pluronic F87 | Clear Single Phase | 10 mm |
| Poloxamer 338 | Pluronic F108 | Clear Single Phase | 6 mm |
| Poloxamer 407 | Pluronic F127 | Clear Single Phase | 7 mm |

From this testing, Poloxamer 188, 338, and 407 give unexpectedly low toxicity while maintaining an acceptable appearance.

EXAMPLE 3

1–20% Poloxamer (polyoxyethylene, polyoxypropylene block polymer) nonionic surfactant with 0.1% Hexylresorcinol as an antiseptic and 0.2% chlorhexidine digluconate as the preservative.

EXAMPLE 4

1–20% Poloxamine (polyoxyethylene, polyoxypropylene block polymer of ethylene diamine) nonionic surfactant with 0.1% Hexylresorcinol as an antiseptic and 0.2% chlorhexidine digluconate as the preservative.

EXAMPLE 5

1–20% Poloxamer (polyoxyethylene, polyoxypropylene block polymer) nonionic surfactant with 0.1% Hexylresorcinol as an antiseptic and 0.2% potassium sorbate as the preservative.

EXAMPLE 6

1–20% Poloxamine (polyoxyethylene, polyoxypropylene block polymer of ethylene diamine) nonionic surfactant with 0.1% Hexylresorcinol as an antiseptic and 0.2% potassium sorbate as the preservative.

EXAMPLE 7

1–20% Poloxamer (polyoxyethylene, polyoxypropylene block polymer) nonionic surfactant with 0.1% Hexylresorcinol as an antiseptic and 0.2% sodium benzoate as the preservative.

EXAMPLE 8

1–20% Poloxamine (polyoxyethylene, polyoxypropylene block polymer of ethylene diamine) nonionic surfactant with 0.1% Hexylresorcinol as an antiseptic and 0.2% sodium benzoate as the preservative.

Those skilled in the art will recognize that, while specific embodiments have been illustrated and described, various modifications and changes may be made without departing from the spirit and scope of the invention.

What is claimed is:

1. A method for cleansing a wound comprising the steps of: irrigating said wound with a low-cytotoxic topical alcohol-free, aqueous solution comprising from about 1% to about 20% by weight of the total solution of a non-cytotoxic surfactant selected from the group consisting of polyoxyethylene and polyoxypropylene block polymer;

a low-cytotoxic antiseptic selected from the group consisting of from about 0.05% to about 0.05% by weight of the total solution of benzenethonium chloride, from about 0.05% to about 0.5% by weight of the total solution of hexylresorcinol, from about 0.05% to about 0.5% by weight of the total solution of methylbenzethonium chloride, from about 0.05% to about 0.5% by weight of the total solution of phenol, from about 8% to about 12% by weight of the total solution of camphor and from about 3% to about 7% by weight of the total solution of phenol, and from about 3% to about 12% by weight of the total solution of camphor and from about 1% to about 4% by weight of the total solution of metacresol; and from about 0.05% to about 2.0% by weight of the total solution of a non-cytotoxic preservative selected from the group consisting of DMDM hydantoin, potassium sorbate, and chlorhexidine digluconate with the proviso that the solution does not contain cytotoxic amounts of benzalkonium chloride as determined by an agarose overlay test; and thereby cleansing said wound.

2. The method of claim 1, wherein said antiseptic is hexylresorcinol and said preservative is chlorhexidine digluconate.

3. The method of claim 2, wherein said antiseptic comprises about 0.05 to about 2.0% by weight of the total solution and wherein said antiseptic is hexylresorcinol.

4. The method of claim 2, wherein said preservative comprises 0.05% to about 2.0% by weight of the total solution and wherein said preservative is chlorhexidine digluconate or a salt of chlorhexidine.

5. A low-cytotoxic topical alcohol-free, aqueous solution for cleansing wounds said solution having a low cytotoxicity as determined by an agarose overlay test, comprising from about 1% to about 20% by weight of the total solution of a surfactant selected from the group consisting of polyoxyethylene and polyoxypropylene block polymer;

an antiseptic selected from the group consisting of from about 0.05% to about 0.5% by weight of the total solution of benzenethonium chloride, from about 0.05% to about 0.5% by weight of the total solution of hexylresorcinol, from about 0.05% to about 0.5% by weight of the total solution of methylbenzethonium chloride, from about 0.05% to about 0.5% by weight of the total solution of phenol, from about 8% to about 12% by weight of the total solution of camphor and from about 3% to about 7% by weight of the total solution of phenol, and from about 3% to about 12% by weight of the total solution of camphor and from about 1% to about 4% by weight of the total solution of metacresol; and from about 0.05% to about 2.0% by weight of the total solution of a preservative selected from the group consisting of DMDM hydantoin, potassium sorbate, and chlorhexidine digluconate with the proviso that the solution does not contain cytotoxic amounts of benzalkonium chloride according to an agarose overlay test.

6. The composition of claim 5, wherein said block polymer further comprises about 1% to about 20% by weight of ethylene diamine.

7. The composition of claim 5, wherein said antiseptic is hexylresorcinol and said preservative is chlorhexidine digluconate.

8. The composition of claim 5, wherein said antiseptic comprises about 0.05 to about 2.0% by weight of the total solution and wherein said antiseptic is hexylresorcinol.

9. The composition of claim 5, wherein said preservative comprises 0.05% to about 2.0% by weight of the total solution and wherein said preservative is chlorhexidine digluconate or a salt of chlorhexidine.

10. A low-cytotoxic topical alcohol-free, aqueous solution for cleansing wounds said solution having a low cytotoxicity as determined by an agarose overlay test, consisting essentially of (a) a surfactant comprising from about 1 to about 20 percent by weight of the total solution wherein the surfactant is selected from the group consisting of polyoxyethylene and polyoxypropylene block polymer;

(b) an antiseptic selected from the group consisting of (i) about 0.05 to about 0.5 percent by the weight of the total solution of a compound selected from the group consisting of benzenethonium chloride, hexylresorcinol, methylbenzethonium chloride, and phenol;

(ii) camphorated phenol comprising about 8 to about 12 percent by weight of the total solution of camphor and about 3 to 7 percent by weight of the total solution of phenol; and (iii) camphorated metacresol comprising about 3 to about 12 percent by weight of the total solution of camphor and about 1 to 4 percent by weight of the total solution of metacresol; and (c) from about 0.05 to about 0.5 percent by weight of the total solution of a preservative selected from the group consisting of DMDM hydantoin, potassium sorbate, and chlorhexidine digluconate.

11. The solution of claim 10 wherein the antiseptic is hexylresorcinol and comprises from about 0.05 to about 0.5 percent by weight of the total solution and wherein the preservative is chorhexidine or a salt thereof and comprises from about 0.05 to about 0.5 percent by weight of the total solution.

* * * * *

UNITED STATES PATENT AND TRADEMARK OFFICE
CERTIFICATE OF CORRECTION

PATENT NO. : 5,762,917
DATED : JUNE 9, 1998
INVENTOR(S) : David W. Osborne

It is certified that error appears in the above-indentified patent and that said Letters Patent is hereby corrected as shown below:

In claim 1, column 4, line 20, delete "about 0.05%" to about 0.05%"; and replace with ---about 0.05% to about 0.5%---.

Signed and Sealed this

Eighteenth Day of August, 1998

Attest:

BRUCE LEHMAN

Attesting Officer

Commissioner of Patents and Trademarks